(12) United States Patent
Ramirez et al.

(10) Patent No.: US 10,222,320 B2
(45) Date of Patent: *Mar. 5, 2019

(54) IDENTIFYING AND ENUMERATING EARLY GRANULATED CELLS (EGCS)

(71) Applicant: Beckman Coulter, Inc., Brea, CA (US)

(72) Inventors: Carlos Ramirez, Miami, FL (US); Jiuliu Lu, Homestead, FL (US)

(73) Assignee: Beckman Coulter, Inc., Brea, CA (US)

( * ) Notice: Subject to any disclaimer, the term of this patent is extended or adjusted under 35 U.S.C. 154(b) by 30 days.

This patent is subject to a terminal disclaimer.

(21) Appl. No.: 15/489,488

(22) Filed: Apr. 17, 2017

(65) Prior Publication Data

US 2017/0219475 A1    Aug. 3, 2017

Related U.S. Application Data

(63) Continuation of application No. 14/110,121, filed as application No. PCT/US2012/032603 on Apr. 6, 2012, now Pat. No. 9,658,215.

(60) Provisional application No. 61/472,974, filed on Apr. 7, 2011.

(51) Int. Cl.
*G01N 15/14* (2006.01)
*G01N 21/53* (2006.01)
*G01N 33/50* (2006.01)
*G01N 21/47* (2006.01)

(52) U.S. Cl.
CPC ....... *G01N 15/147* (2013.01); *G01N 15/1429* (2013.01); *G01N 21/53* (2013.01); *G01N 33/5094* (2013.01); *G01N 2021/4707* (2013.01); *G01N 2021/4769* (2013.01)

(58) Field of Classification Search
None
See application file for complete search history.

(56) References Cited

U.S. PATENT DOCUMENTS

| 5,125,737 | A  | 6/1992  | Rodriguez et al. |
|-----------|----|---------|------------------|
| 5,389,549 | A  | 2/1995  | Hamaguchi        |
| 5,538,893 | A  | 7/1996  | Sakata           |
| 5,677,183 | A  | 10/1997 | Takarada         |
| 6,004,816 | A  | 12/1999 | Mizukami         |
| 6,916,658 | B2 | 7/2005  | Li et al.        |
| 7,374,937 | B1 | 5/2008  | Prockop et al.   |
| 7,625,712 | B2 | 12/2009 | Paul et al.      |
| 9,658,215 | B2 | 5/2017  | Ramirez et al.   |
| 2005/0255447 | A1 | 11/2005 | Ortiz         |
| 2005/0260766 | A1 | 11/2005 | Paul et al.   |
| 2009/0297471 | A1 | 12/2009 | Markovic et al. |

FOREIGN PATENT DOCUMENTS

| WO | 1988/007198 A1 | 9/1988  |
| WO | 2012/139047 A2 | 10/2012 |

OTHER PUBLICATIONS

Loken et al., Analysis of cell populations with a fluorescence-activated cell sorter. Annals New York Academy of Sciences, 254:163-171 (1975).
Polyakova et al., Detection of dyaplastic neutrophils and abnormal lymphocytes with cell population data on the unicel DxH800 coulter cellular analysis system. International Journal of Laboratory Hematology, 33 (Suppl. 1), Poster Abstract 140, p. 74 (2011).
Piccinini et al., Cell population data and MAF of coulter unicel DxH 800 in the detection and differentiation of dysplastic granulocytes. International Journal of Laboratory Hematology, 33 (Suppl. 1), Poster Abstract 137, p. 73 (2011).
International Search Report and Written Opinion for PCT/US2012/032603 filed on Apr. 6, 2012.
Morstyn et al., Purification of hemopoietic progenitor cells from human marrow using a fucose-binding lectin and cell sorting. Blood, 56(5):798-805 (1980).
Grogan et al., Electronic sorting of granulocyte precursor cells from stimulated bone marrow. J. Histochem. Cytochem., 27(6):1011-1016 (1979).
Goldschneider et al., Analysis of rat hemopoietic cells on the fluorescence-activated cell sorter. J. Exp. Med., 152:419-437 (1980).

*Primary Examiner* — Thomas J. Visone
(74) *Attorney, Agent, or Firm* — K&L Gates LLP; Louis C. Cullman; Georgia N. Kefallinos

(57) ABSTRACT

Methods and systems for automatically identifying and enumerating early granulated cells (EGC) in blood samples are disclosed. In one embodiment a method for identifying EGC in a blood sample includes analyzing white blood cells of the blood sample using a low angle light scatter (LALS) parameter, separating the EGCs from the other white blood cells using the LALS parameter, and enumerating the separated EGCs.

9 Claims, 9 Drawing Sheets

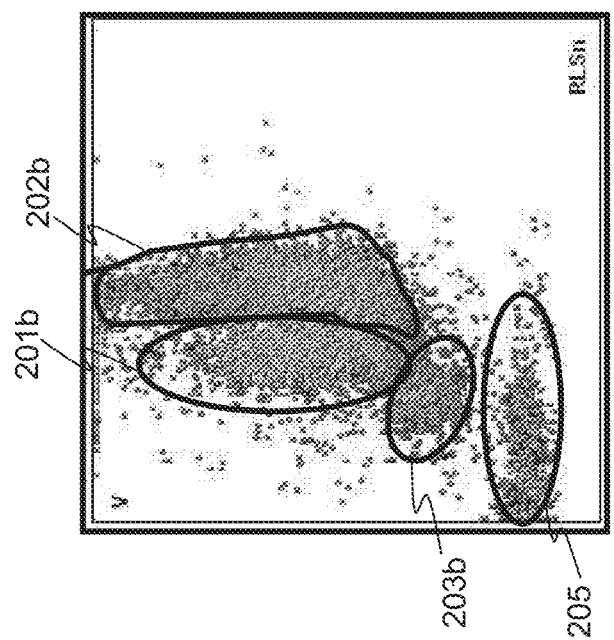
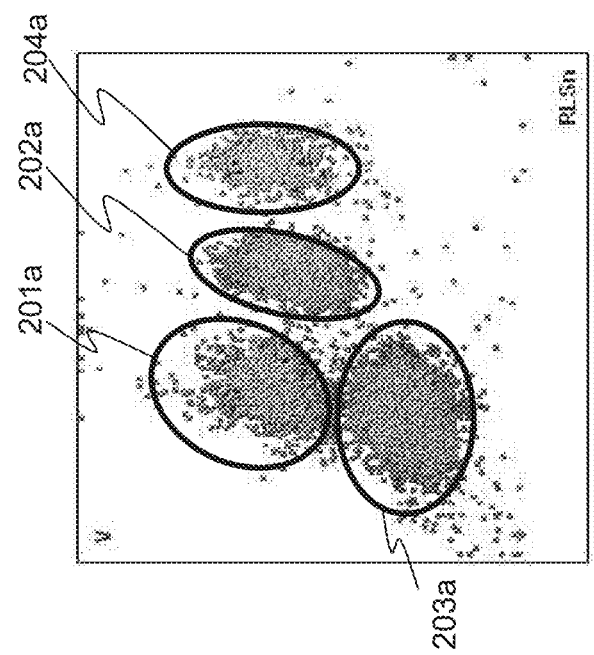

IDENTIFYING AND ENUMERATING EARLY GRANULATED CELLS (EGCS)

CROSS REFERENCE TO RELATED APPLICATIONS

This application is a continuation of U.S. patent application Ser. No. 14/110,121 filed on Oct. 17, 2013, which claims priority under 35 U.S.C. § 371 to International Patent Application PCT/US2012/032603 filed on Apr. 6, 2012, which claims the benefit of U.S. Provisional Application No. 61/472,974, filed on Apr. 7, 2011, both of which are incorporated herein by reference in their entirety.

BACKGROUND

Field of the Invention

Embodiments of the present specification relate in general to the analysis of cellular event data generated by a particle analyzer, and more particularly to detecting and enumerating Early Granulated Cells (EGCs) in blood samples.

Background

Particle analyzers are used to analyze biological cell samples so as to determine the count and/or distribution of one or more types of cells contained in the samples. Particle analyzers include hematology analyzers and flow cytometers. Hematology analyzers and flow cytometers measure and differentiate blood cells of various types by collecting and analyzing signals produced when the cells pass through a small aperture or measurement region that is monitored by one or more sensors. For example, a sample of blood is flowed through a measurement region in which one or more energy sources and associated sensors are configured to detect signals corresponding to various physical characteristics of the cells that pass through. One or more of the signals corresponding to the measurements of a single cell in the measurement region is referred to as a cellular event. Cellular event data for a plurality of cells of a cell sample are then analyzed to determine populations differentiated based upon physical characteristics of the cells.

Measurements of physical properties, such as volume, conductivity, and light scatter, are used to classify cells. For example, Volume, Conductivity and Scatter (VCS) technology from Beckman Coulter is used, among other applications, to classify white blood cells into subgroups or populations. These physical measurements form a multidimensional space where cells sharing similar physical properties group into clusters. Each cluster corresponds to a population of a specific type of blood cells.

The enumeration of white blood cells (WBCs, also referred to as leukocytes) is an important tool for detecting pathological conditions such as various forms of infection. The 5-part WBC Differential has for long been an invaluable test in the detection of hematological conditions. The 5-part Differential detects and enumerates the five major subtypes of WBC that are normally found in the peripheral blood, i.e., neutrophils, lymphocytes, monocytes, eosinophils and basophils. However, there can be other types of WBC in intermediate stages of the maturation process. These WBC that are in intermediate stages of the maturation process include blast cells, variant lymph cells, and Early Granulated Cells (EGCs), that are also indicators of hematology disorders. The term EGC refers to a subset of immature myeloid cells mainly composed of promyelocytes, myelocytes, and metamyelocytes. Other cells in intermediate stages of maturation, such as, blast cells and band cells are generally not included in the EGC population.

The elevated presence of EGCs in the peripheral blood might indicate enhanced bone marrow activation. The count of EGCs, for example, can be indicative of sepsis which is a severe form of bacterial infection. In general, an increase in circulating EGCs occurs during bacterial infection. The presence of EGCs indicates increased myeloid cell production due to infection or severe inflammatory disease. EGCs can also be found in patients with leukemia, myelodysplastic syndrome, and myelofibrosis. Thus, rapid and accurate enumeration of the EGCs in a patient's blood sample can be highly desirable for the timely treatment of acute infections, sepsis, and other conditions. Enhancing the routine 5-part WBC Differential test by adding an EGC count can offer substantially increased diagnostic capabilities.

In conventional methods of analysis, the presence of EGCs is associated with changes in the shape of a cell event population in a two dimensional histogram or scattergram. Based on the shape of one or more cell populations, conventional particle analyzers are capable of alerting the end user about the presence of immature or atypical cells.

EGC enumeration is conventionally done by means of manual blood smear analysis. This process is labor intensive and is highly prone to error due to various factors such as the low number of cells counted and human subjectivity.

Another conventional method of EGC enumeration is based on fluorescence. The WBC are stained with a polymethine dye which stains the RNA and DNA of each cell. EGCs can then be identified apart from mature granulocytes based upon the higher fluorescence due to the larger content of RNA and DNA in the EGCs. However, fluorescence based technology can be expensive and may not be suitable for relatively low cost analyzers. Therefore, there is a need to be able to determine EGC by a non fluorescent method and instrument.

Still further, another method has been disclosed that measures immature granulocytes on the basis of only DC. However, the accuracy of this measurement might be compromised in cases wherein the volumes of the neutrophil subpopulation, immature granulocyte subpopulation and bands overlap.

Yet another conventional method of EGC enumeration involves flow cytometric analysis using one or more antibodies, such as, for example, the CD16 antibody. Using this method EGCs can be identified based upon the lack of CD16 staining on EGC cells. However, the method involves the use of multiple antibodies to sequentially gate different cell types. Therefore, the flow cytometric methods using antibodies to identify EGCs can be cost prohibitive and can cause changes in the physical characteristics of the cells due to the use of one or more antibodies.

Accordingly, there remains a need for efficient methods and systems to identify and enumerate EGCs in blood samples.

BRIEF SUMMARY

Methods and systems for automatically identifying and enumerating Early Granulated Cells (EGCs) in blood samples analyzed in a particle analyzer are disclosed. In one embodiment a method for identifying EGC in a blood sample includes analyzing white blood cells of the blood sample using a low angle light scatter (LALS) parameter, separating the EGCs from the other white blood cells using the LALS parameter, and enumerating the separated EGCs.

Another embodiment is an apparatus for identifying EGC in a blood sample. The apparatus includes, a processor, at least one memory coupled to the processor, and an EGC determiner module. The memory is configured to store cellular event data from a particle analyzer, the cellular event data including a LALS parameter. The EGC determiner module is configured to analyze white blood cells of the blood sample using the LALS parameter, and to differentiate and/or separate a population of EGCs from other white blood cells based upon the LALS parameter.

Further features and advantages of the present specification, as well as the structure and operation of various embodiments thereof, are described in detail below with reference to the accompanying drawings. It is noted that the specification is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Further features and advantages of the present specification, as well as the structure and operation of various embodiments thereof, are described in detail below with reference to the accompanying drawings. It is noted that the specification is not limited to the specific embodiments described herein. Such embodiments are presented herein for illustrative purposes only. Additional embodiments will be apparent to persons skilled in the relevant art(s) based on the teachings contained herein.

FIGS. 2a and 2b illustrate scattergrams of WBC differential analysis based on volume and light scatter. FIG. 2a illustrates a normal sample. FIG. 2b illustrates a sample with EGCs.

FIG. 3a illustrates a scattergram based on volume and rotated medium angle light scatter. FIG. 3b illustrates a scattergram based on volume and conductivity.

FIG. 4a illustrates a scattergram with conductivity and LALS. FIG. 4b illustrates a scattergram with conductivity and a derived measurement that includes LALS. FIG.4c illustrates a scattergram with a first derived measurement that includes LALS and a second derived measurement that includes Opacity(OP).

Figure 1:
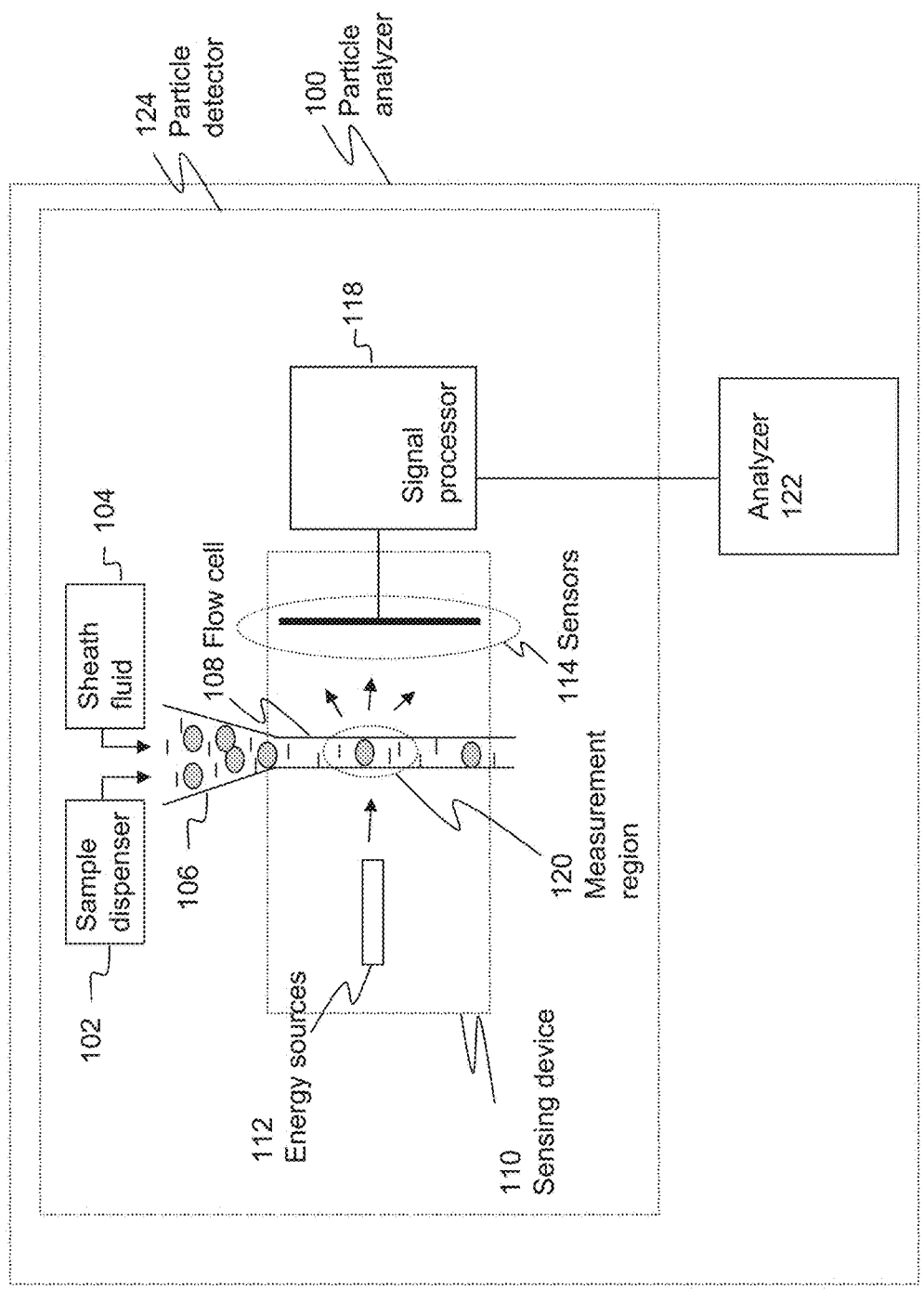
FIG. 1 is a system according to an embodiment of the present specification.

The features and advantages of the present specification will become more apparent from the detailed description set forth below when taken in conjunction with the drawings. In the drawings, like reference numbers generally indicate identical, functionally similar, and/or structurally similar elements. Generally, the drawing in which an element first appears is indicated by the leftmost digit(s) in the corresponding reference number.

DETAILED DESCRIPTION

The present specification relates to the processing and analysis of cellular event data generated by a particle analyzer. While the present specification is described herein with reference to illustrative embodiments for particular applications, it should be understood that the specification is not limited thereto. Those skilled in the art with access to the teachings herein will recognize additional modifications, applications, and embodiments within the scope thereof and additional fields in which the specification would be of significant utility.

Overview

As described above, the detection and enumeration of Early Granulated Cells (EGCs) is of great diagnostic value to detect a range of hematological conditions. The methods and systems disclosed herein enable the identification and enumeration of EGCs in cell samples by analyzing cellular event data generated by a particle analyzer. The present specification provides a superior approach to existing techniques in that the present specification does not require any special or expensive dyes, stains, or antibodies to separate the EGCs from the generally overlapping neutrophil population.

As used herein, the terms "parameter" and "measurement" are generally used interchangeably. In regards to the present specification, a laser emits a beam of energy that is reflected or deflected from a particle, i.e., a cell, and that energy is measured as a parameter by one or more detectors. Therefore, it is generally considered that the energy is a measured parameter. Certain parameters are not directly measured, but rather are calculated. By way of specific example, Opacity (OP) and RMALS are calculated parameters from the measured DC and RF for Opacity parameter and MALS and DC for the RMALS parameter.

Embodiments of the present specification utilize low angle light scatter (LALS) measurements to automatically detect and enumerate EGC populations in blood samples. Furthermore, the enumeration of EGC according to embodiments of the present specification does not require repeat testing of the sample in the particle detector. The enumerated EGC information can either be incorporated as part of the 5-part Differential test for white blood cells, or be presented separately.

Exemplary environments in which this specification may be practiced include particle analyzers such as flow cytometers and hematology analyzers. The DxH 800™ hematology analyzer, for example, uses a variation of the Coulter proprietary Volume, Conductivity, and Scatter (VCS) technology to interrogate cells inside a measurement region of a particle analyzer. VCS uses at least three independent energy sources that work in concert with each other to interrogate cells: a low frequency direct current (DC) power source to measure volume; a high frequency power source to measure conductivity (OP), and one or more laser light sources to measure scatter. The volume measurement is performed using the Coulter Principle of electrical impedance to physically measure the volume that the entire cell displaces in an isotonic diluent. This method accurately sizes all cell types regardless of their orientation in the light path. Alternating current in the radio frequency (RF) range short circuits the bipolar lipid layer of a cell's membrane, allowing the energy to penetrate the cell. This energy source is used to collect information about cell size and internal structure, including chemical composition and nuclear volume. One or more laser energy sources and multiple-angle light scatter sensors or detectors provide information about a cell's internal structure, granularity, and surface morphology. Light scatter measurements can include upper medium angle light scatter (UMALS) measured, for example, in a range between 20-65 degrees from the axis, lower medium angle light scatter (LMALS) measured, for example, in a range between 10-20 degrees from the axis. The combination of UMALS and LMALS is commonly referred to as MALS, but UMALS and LMALS constitute separate light scatter measurements using adjoining light detectors.

In addition, VCS instruments use the highly accurate DC measurement of volume, to obtain other measurements that are adjusted for cell size from conductivity and scatter. U.S. Pat. No. 5,616,501 (to Rodriguez et al), which is hereby incorporated by reference in its entirety, contains a detailed description of a particle analyzer and the use of VCS technology.

In addition to the above measurements, DxH 800™ hematology analyzer also includes a LALS measurement and an axial light loss measurement (ALL or AL2). LALS is measured, for example, in a range between 0-10 degrees from the axis. ALL is measured as the light loss along the axis, for example, at 0-1.0 degrees from the axis. A person of skill in the art would understand, however, that the exemplary light scatter angles corresponding to UMALS, LMALS, LALS, and ALL are relative to each other, and can change due to factors such as individual characteristics of the particle detector and reagents or other materials mixed with the cell samples. It should be noted, however, that the teachings in this disclosure are not limited to devices using VCS technology or its variants.

FIG. 1 illustrates a particle analyzer 100 according to an embodiment of the present specification. FIG. 1 is for illustrative purposes only, and it should be understood that particle analyzers can include more or fewer modules, different modules, and different designs than shown in FIG. 1. Particle analyzer 100 includes a particle detector 124 and an analyzer 122. Particle detector 124 includes a particle sample dispenser 102 and a sheath fluid dispenser 104. Sample dispenser 102 includes a particle sample prepared according to the requirements of a desired analysis or test. For example, a sample of blood may be diluted with a diluent to a predetermined degree of cell concentration. The type of diluent and the degree of dilution differ according to the test being run—white blood cell (WBC) analysis requires less dilution than red blood cells (RBC) because the number of WBC in a sample is low compared to RBC. A sheath fluid dispenser 104 holds a sheath fluid such as, for example, saline. The sheath fluid enables the smooth flowing of the particle sample in the particle detector. The particle sample from particle sample dispenser 102 and the sheath fluid from sheath fluid dispenser 104 are injected at a predetermined constant rate. Solution dispenser 106 funnels the particle sample and sheath fluid into a flow cell 108. Flow cell 108 is, in general, a tube of a small diameter designed for a single particle to pass through. The solution in solution dispenser 106 is injected into flow cell 108 at a constant rate through hydrodynamic focusing. Hydrodynamic focusing injects the solution at a constant rate and under sufficient pressure that, in general, the particles appear in single-file at constant intervals within flow cell 108. It should be noted that some particle detectors can have a measurement area without a flow cell.

A sensing device 110 is positioned within particle detector 124 such that one or more sensing mediums may be employed to sense particles flowing through measurement region 120. Energy sources 112 and associated sensors 114 are positioned within sensing device 110 substantially transversely to flow cell 108. Energy sources 112 and sensors 114 employ one or more of electrical or optical sensing mediums to detect particles in measurement region 120. For example, a set of energy sources 112 and associated sensors 114 can employ a light measurement to measure the light scatter and light loss characteristics of a cell passing through measurement region 120. Light scatter measurements can include UMALS, LMALS, and LALS. Light loss is measured as the axial light loss (ALL or AL2), i.e., light loss along the axis, for example, at 0-1.0 degrees from the axis. Other sets of energy sources 112 and sensors 114 can employ a DC measurement to measure the volume (V) of a cell, and an RF measurement to measure the conductivity (OP) characteristics of a cell. Energy sources 112 and sensors 114 can also include other mediums, such as, for example, an acoustic medium where ultrasound is used to detect various characteristics of a cell in measurement region 120.

Sensors 114 are coupled to a signal processor 118. Sensors 114 convert detected electrical or optical measurements to corresponding electrical signal pulses that are processed in signal processor 118. For each particle passing through measurement region 120, electrical signal pulses corresponding to a sequence of measurements are collected, for example, in signal processor 118. From these electrical signal pulses a signal is formed that is illustrative of the measurements captured for one measurement parameter while one particle is flowing through the measurement region. The input to the signal processor 118 can be analog or digital signal. One or more analog to digital converters (ADC) can be used to convert the analog signals to digital before, during, or after the processing in the signal processor 118. The duration covered by the signal can commence upon the entry of the particle into the measurement region to its exit from the measurement region. In embodiments of the present specification, signal processor 118 may perform additional processing of each signal to derive one or more measurement parameters describing the particle that was detected.

The detection of a particle within measurement region 120 is referred to as an event or cellular event. Signal processor 118 analyzes the derived signal corresponding to each detected particle flowing through measurement region 120 to determine a corresponding event. Detected events are then transmitted to analyzer 122. Analyzer 122 is coupled to signal processor 118 to receive event data. Analyzer 122 can be located in a computer coupled to the particle detector. It should be noted that analyzer 122 can either be located on-board the particle analyzer 100 comprising particle detector 124, or separately being coupled to particle analyzer 100 through a communication infrastructure.

Signal generation and event detection is performed separately for each active electrical or optical measurement separately. Analyzer 122 can receive event data corresponding to each active measurement. Analyzer 122 can then analyze the received event data to determine one or more counts, cell populations, or other characteristic corresponding to the cell. In embodiments of the present specification, analyzer 122 can cause the display of scatter plots, histograms, or other graphical and/or textual illustrations of the received events. The scatter plots, histograms, and/or other graphical representations can be multi-dimensional.

"Sensitivity" and "specificity" are statistical measures of the performance of a binary classification test. Sensitivity measures the proportion of actual positives which are correctly identified. Specificity measures the proportion of negatives which are correctly identified. A specificity of 100% means that the test recognizes all actual negatives. A sensitivity of 100% means that the test recognizes all actual positives. Thus, in contrast to a high specificity test, negative results in a high sensitivity test are used to rule out the disease. A positive result in a high specificity test can confirm the presence of disease. However, specificity alone does not sufficiently indicate accuracy of the test to recognize positive cases. Knowledge of sensitivity is also required. For any test, there is usually a trade-off between these measurements. For example, in a diagnostic assay in which one is testing for people who have a certain condition, the assay may be set to overlook a certain percentage of sick people who are correctly identified as having the condition (low specificity), in order to reduce the risk of missing the percentage of healthy people who are correctly identified as not having the condition (high sensitivity). This trade-off can be represented graphically using a receiver operating characteristic (ROC) curve.

The "accuracy" of a measurement system is the degree of closeness of measurements of a quantity to its actual (true) value.

In one embodiment, the specification discloses a method for enumerating EGCs with at least about 80% accuracy, and more particularly with at least about 85% accuracy. In preferred embodiments, the specification discloses a method for enumerating EGCs with at least about 90% accuracy.

In another embodiment, the specification discloses a method for enumerating EGCs with at least about 85% sensitivity, more particularly with at least about 90% sensitivity, and even more particularly with at least about 95% sensitivity. In still another embodiment, the specification discloses a method for enumerating EGCs with at least about 80% specificity, and more particularly with at least about 85% specificity. In preferred embodiments, the specification discloses a method for enumerating EGCs with at least about 90% specificity.

Use of LALS to Identify and Enumerate EGC

The inventors observed that EGCs can be differentiated from other cell types, including specifically neutrophils, on the basis of their unique aspects of granularity, nuclear lobularity, and/or cell surface structure. These unique aspects, the inventors discovered, can be measured and used as basis to identify the EGC population. In one specific embodiment, LALS can be used to discern the degree of a cell's granularity, nuclear lobularity, and/or cell surface structure. Specifically, the present inventors have discovered that the LALS parameter is highly sensitive to subtle changes in granularity, lobularity and/or surface features of ECGs as compared to mature WBCs. However, it is also understood that LALS can be combined with other parameters for specificity and sensitivity in enumeration of EGCs. More particularly, an embodiment of the present specification includes a non fluorescent method and instrument which measures EGCs using LALS and at least one measurement from the group of forward light scatter, side scatter, axial light loss, DC, RF and Opacity. Still further, the forward scatter light is selected from UMALS, LMALS, MALS.

FIGS. 2a and 2b illustrate a WBC differential scattergram from a normal blood sample (FIG. 2a) and a blood sample containing EGCs (FIG. 2b). Populations 202a and 202b represent the neutrophil populations respectively of the normal sample and the sample containing EGCs. The shape of populations 202b is elongated along the volume axis when compared to the shape of population 202a. Populations 201a and 201b represent monocytes, populations 203a and 203b represent lymphocytes, population 204 represents eosinophils, and population 205 represent unlysed RBCs. Many conventional methods identify the presence of EGC based on the elongation of the shape of the neutrophil population, such as that shown in FIG. 2b. FIGS. 19 and 20 of U.S. Pat. No. 5,125,737 (to Rodriguez et al), for example, illustrate the elongation of the shape of the neutrophil population along the volume or DC axis in scattergrams respectively mapping DC vs. OP and DC vs. RMALS. RMALS is rotated medium angle light scatter is typically calculated as log(UMALS+LMALS)/DC.

Figure 3B:
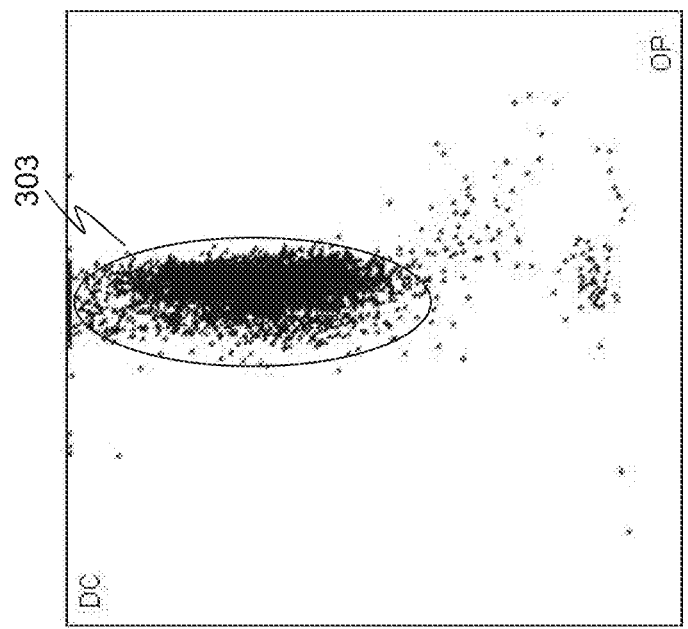
FIGS. 3a and 3b illustrate the overlapping of neutrophil and EGC populations.
Figure 3A:
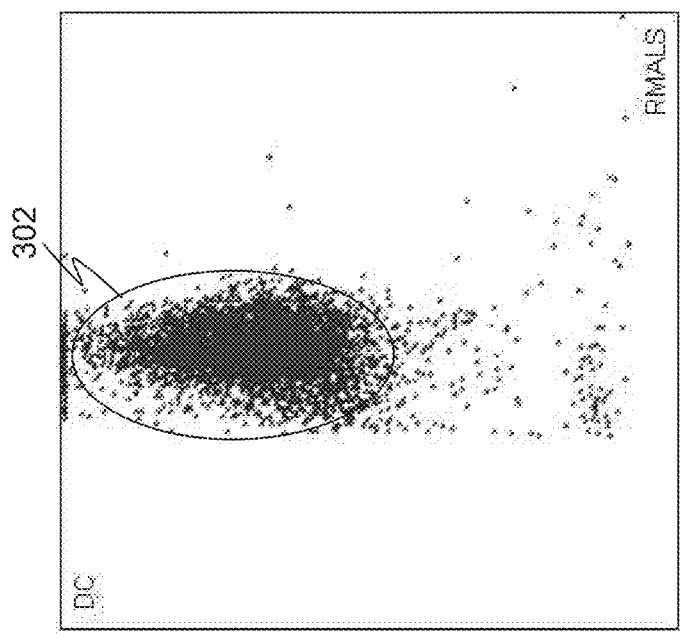

FIGS. 3a and 3b illustrate, respectively, DC vs. RMALS and DC vs. OP scattergrams of another blood sample. The blood sample illustrated in FIGS. 3a and 3b includes a manual reference of 62.25% segmented neutrophils, 12.75% bands, 3% metamyelocytes, and 0.75% myelocytes. In both scattergrams, as seen in clusters 302 and 303, the EGC population cannot be separately identified from the neutrophil population. Therefore, although the elongation of the shape of the neutrophil population can be used as an indicator as to the presence of EGC in the blood sample, the scattergrams based upon DC, RMALS, and OP, as used conventionally, do not separately identify an EGC population and/or enumerate the EGC.

Figure 4A:
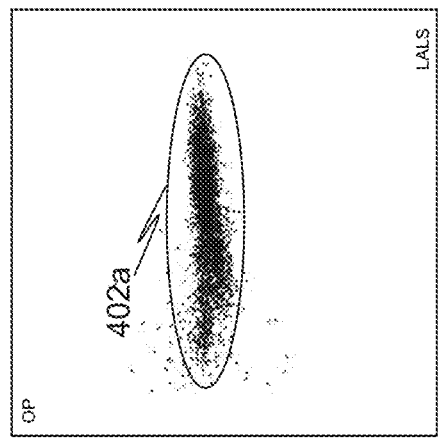
FIGS. 4a, 4b, and 4c illustrate using LALS to detect the EGC population, according to embodiments of the present specification.

FIG. 4a is an illustration of a scattergram mapping OP vs. LALS in accordance with an embodiment of the present specification. Cluster 402 illustrates in a scattergram of OP vs. LALS, the same cellular events shown in FIGS. 3a and 3b. The elongation of the shape of the population 402 along the LALS axis enables the flagging of the sample for the presence of EGC.

Embodiments of the present specification use LALS to identify EGC populations. Described below are embodiments in which LALS is combined with other parameters, such as MALS, ALL, OP and/or DC, to identify and enumerate EGC populations. LALS can be combined with other parameters and/or derived parameters including LALS derivatives to identify the EGC population. It is understood that LALS can be used according to various other combinations of parameters or derived parameters to identify and enumerate EGC based upon the teachings in this disclosure. The present specification, however as previously mentioned, is not limited solely to the use of LALS to identify and enumerate EGCs because the LALS parameter is only one way of detecting the granularity, lobularity, and/or cell surface features of EGCs. These cell features are what allowed the present inventors to discern the EGCs from their closely overlapping neutrophil populations.

Combining LALS with MALS to Identify and Enumerate EGC

According to another embodiment of the present specification, LALS can be used with one or more of MALS and DC and RF to identify and enumerate EGC. According to an embodiment, the LALS is used with MALS and DC. In a further embodiment, OP can be used to more clearly differentiate the EGC population from other cell populations such as neutrophils. A still further embodiment uses LALS, MALS, OP, and DC in constructing derived parameters to differentiate the EGCs.

It is understood that derivative functions are known ways to enhance subtle difference in closely related populations. The selection of a derivative function and the attendant variables or additional parameters is well within the level of skill for a person working in this field. In the Figures, OP, RLS, F1, F2, P1 and P2 are derived functions.

In one embodiment, a derived parameter which incorporates LALS and DC to differentiate EGCs from neutrophils based on the distinctive nuclear lobularity and surface structure properties of EGCs and neutrophils. EGCs have lower LALS compared to neutrophils. In addition, the DC measurement is utilized in the derived measurement to increase the separation between EGCs and neutrophils based upon the characteristic that EGCs are usually larger in size than neutrophils. For example, FIG. 19 of U.S. Pat. No. 5,125,737 illustrates that EGCs have a larger volume than neutrophils.

In a further embodiment, a derived measurement can incorporate OP (which is a function of RF and DC) to increase the separation of EGCs from neutrophils. EGCs have lower OP as compared to neutrophils.

In certain embodiments, the derived parameter can also incorporate MALS. MALS contributes to increase the separation between EGCs and neutrophils by sensing subtle structural differences at medium angle of light scatter. However, as seen in FIG. 3a, MALS alone cannot achieve a distinctive separation between the EGC and neutrophil populations.

Figure 4B:
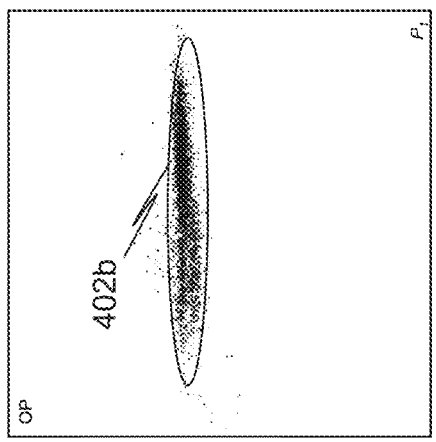
Figure 4C:
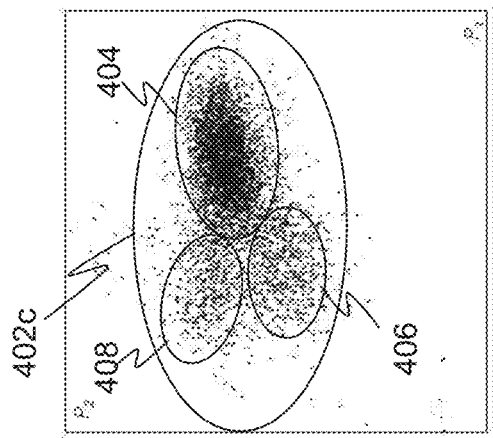

FIGS. 4b and 4c show the cell sample of FIG. 4a when derived parameters are incorporated to create scattergrams. FIG. 4b shows the elongation of the neutrophil population 402b along the P1 axis. FIG. 4c shows the spreading of the neutrophil population 402c relative to the P2 axis, when that derived measurement is introduced. The final result of applying the exemplary embodiments to a blood sample, as shown in FIG. 4c, can yield a scattergram in which EGCs can be distinctly recognized apart from neutrophils. In FIG. 4c, the EGC population 406, is sufficiently distinct from the neutrophil population 404 and undefined population 408. In the illustrated scattergram, the EGC population 406 accounts for 8.8% of the WBC population, and the undefined population 408 accounts for 7.8% of the WBC population. The EGO population appears to be almost entirely comprised of metamyelocytes, myelocytes, and promyelocytes. In some instances, a small percentage of myeloid blast cells in their transition to the promyelocyte stage can be included in the EGC population. The undefined population appears to comprise of degranulated neutrophils, aged neutrophils, and bands.

In arriving at the derived parameters of the disclosed embodiments, it is understood that appropriate coefficient values can be a combination of coefficients that yield a substantially optimal separation among the populations of a cell sample. The selection of coefficient values can be dynamically calculated. For example, according to an embodiment, the coefficient values can be repetitively recalibrated until a predetermined set of thresholds are met with regarding the separation between cell populations mapped on a scattergram.

Combining LALS with ALL to Identify EGC

In another embodiment of the present specification LALS can be considered together with the ALL measurement. The magnitude of the ALL of a cell is representative of its surface properties and absorbance characteristics. U.S. Pat. No. 7,008,792, which is hereby incorporated in its entirety by reference, provides a description of ALL measurement as part of a method to enumerate NRBCs.

The inventors observed that LALS and ALL parameters move in opposite directions for EGCs and neutrophils. Therefore, according to an embodiment of the present specification, a derived measurement based upon LALS and ALL, in particular the difference between LALS and ALL, is created. Considering the difference between LALS and ALL contributes to increasing the separation between the EGO and neutrophil populations.

The inventors also observed that, in general, EGCs exhibit higher DC and lower OP parameters as compared to neutrophils. Thus, according to an embodiment of the present specification, a derived measurement based upon the difference between OP and DC is considered to increase the separation of the EGC population from the neutrophil population.

Additional translation, rotation, and scaling can be performed on the initial derived parameters in order to arrive at an optimized positioning of the EGC and neutrophil populations.

Intermediate derived parameters can further be stretched and scaled to occupy the desired display area. The stretching and scaling contribute to increasing the separation among the populations so that automatic gating and enumeration can be more accurately accomplished.

The derived parameters can be used to generate histograms, scattergrams, and/or other graphical displays in which the EGC and neutrophil populations are separated sufficiently such that automated enumeration of the respective populations can be achieved.

Figure 5:
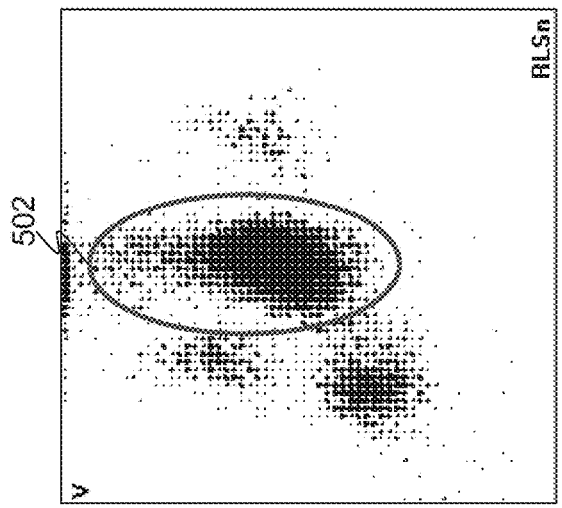
FIG. 5 illustrates a cell population in a DC v MALS scattergram.

FIG. 5 illustrates a neutrophil population 502 that includes EGO in a conventional DC vs. MALS scattergram. As illustrated, the conventional DC vs. MALS scattergram does not sufficiently separate the EGC population from the neutrophil population.

Figure 6:
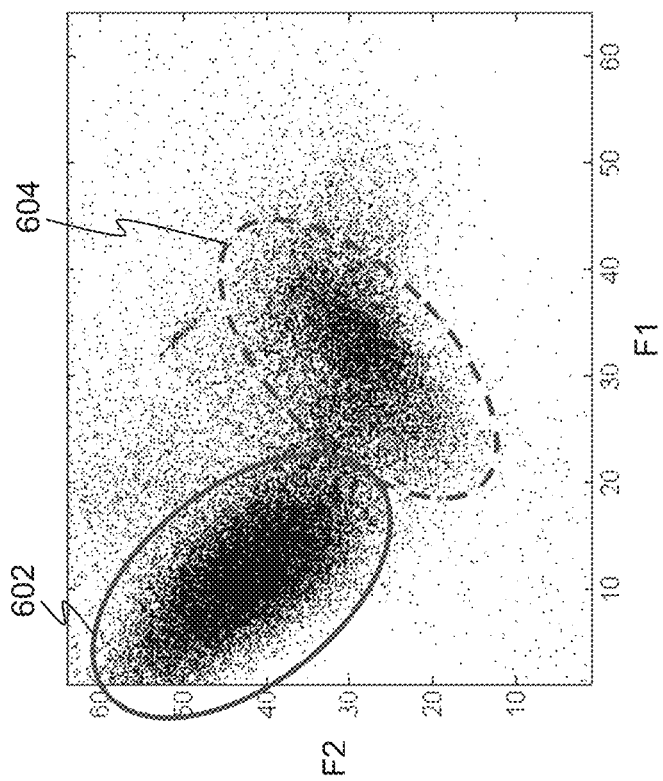
FIG. 6 illustrates the same cell sample of FIG. 5 in a scattergram with derived measurements according to an embodiment of the present specification.

FIG. 6 illustrates the same cell sample as shown in FIG. 5, in a scattergram plotting the derived parameters according to an embodiment of the present specification. In FIG. 6, the EGC population 604 is clearly separated from the neutrophil population 602.

Method to Identify and Enumerate EGC using LALS

Figure 7:
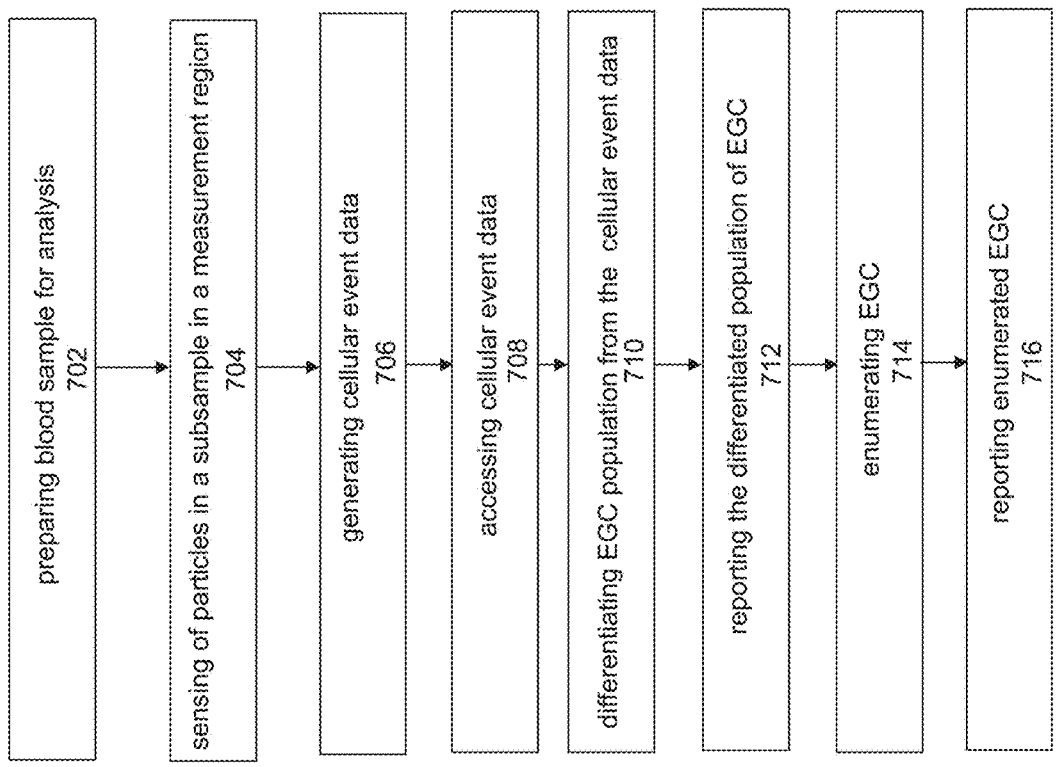
FIG. 7 illustrates a method of detecting and enumerating EGC according to an embodiment of the present specification.

FIG. 7 illustrates a method 700 to identify and enumerate EGCs in a blood sample according to an embodiment of the present specification. Method 700 can be implemented in a particle detector and analyzer such as that illustrated in FIG. 1.

In step 702, a blood sample is prepared for analysis. For example, and without loss of generality, in hematology analysis a whole blood sample can be lysed to remove red blood cells prior to a 5-part Differential test for white blood cells. The preparation step can also include adding a diluent to the sample and optionally a sheath fluid to facilitate the flowing of the sample through a measurement region. The prepared particle sample is then injected into a path including the measurement region at a substantially constant rate using a process such as hydrodynamic focusing to ensure sufficient pressure to move the particles in a single-file through the path.

In step 704, the cells of the blood sample are subjected to measurement in a measurement region of the particle analyzer. The cells in a diluent, and optionally in a sheath fluid, pass one by one through a measurement region. During the time interval that a cell is in the measurement region, a plurality of energy sources and sensors operate to subject the cell to interrogation and to collect the signals generated by the respective interrogations. As described above, according to an embodiment of the present specification a plurality of energy sources and corresponding sensors operate to collect measurement signals for a LALS measurement and one or more of DC, OP, MALS, and ALL parameters.

In step 706, cellular event data corresponding to the collected measurement signals are generated. For example, the cellular event data for a cell can comprise data representing all the parameters of that cell during the interval in which that cell passed through the measurement region. Generating cellular event data can include the generation of electrical signals for optical, RF and other signals detected at the various sensors.

In step 708, the cellular event data is accessed, for example, by an analyzer component. According to an embodiment, some or all of the processing of steps 708-716 can be performed on a real-time or near real-time manner as the cells are measured in the particle detector. According to another embodiment, processing of steps 708-716 can be performed on stored measurement data which have been generated previously by the particle detector.

In step 710, a population of EGC is differentiated from the cellular event data according to an embodiment of the present specification. The differentiation of the EGC population is further described below in relation to FIG. 8.

In step 712, the differentiated population of EGC can be reported. According to an embodiment, reporting includes the display and/or printed output of one or more cell populations in one or more histograms, scattergrams, or other graphic and/or textual form of display. According to another embodiment, reporting includes writing the various cell population data to a computer readable storage medium in order that that stored information is available for later retrieval and analysis.

In step 714, the EGCs are enumerated. After the EGC population is separated from the rest of the cell populations including the neutrophil population, the EGC can be counted. Counting of the EGC can be based on counting individual cellular events that fall within an area, gating the cell events in an area, and/or estimating the cellular events in an area.

In step 716, the enumerated EGC are reported. The enumerated EGC can be reported as an absolute count and/or as a percentage of the total white blood cell count. The enumerated EGC can also be reported as a percentage and/or fraction of any other cell population, such as, for example, neutrophils. As in the case of reporting the differentiated EGC population, the reporting can include display, printed output, and/or storing to a computer readable medium.

Figure 8:
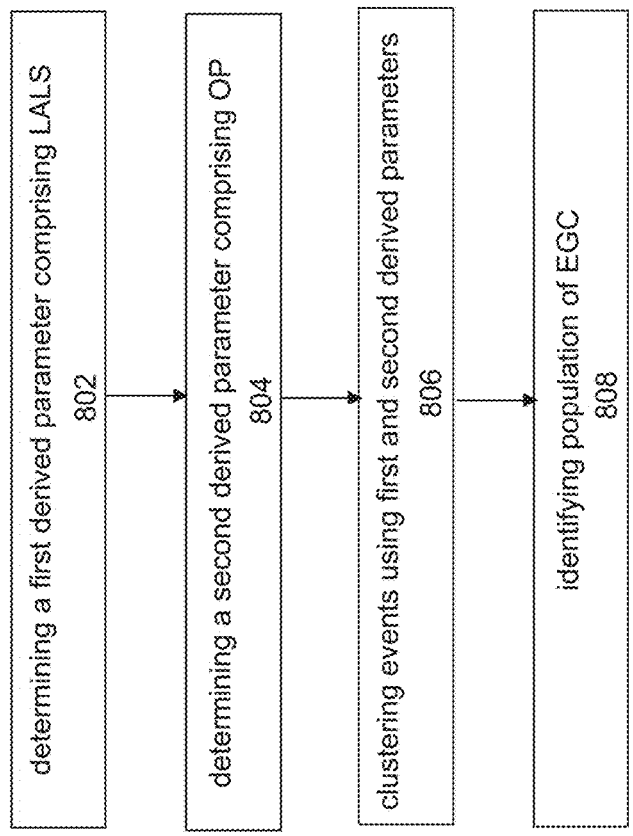
FIG. 8 illustrates a method of identifying a population of EGC according to an embodiment of the present specification.

FIG. 8 illustrates a method 800 to differentiate the EGC population from other cellular populations of the cell sample.

In step 802, a first derived measurement comprising LALS is created. According to an embodiment, a first derived parameter comprises the LALS measurement and a DC measurement.

In step 804, a second derived measurement comprising OP is created. According to an embodiment, a second derived parameter comprises the OP measurement and an MALS measurement.

In step 806, clustering of cellular events is performed. According to an embodiment, a scattergram having the first measurement as one axis, and the second measurement as another axis is created. The clustering of cell populations can be performed manually and/or automatically. The clustering can include iteratively calibrating the coefficients and/or measurement terms until selected cell populations are separated by at least a predetermined threshold distance. The clustering step can also include gating one or more cell populations.

In step 808 the population of EGC is identified based upon the clustering performed in the previous step. The cluster of EGC can be differentiated from the cluster of neutrophils based on the first and second derived parameters as shown in FIG. 4c.

According to another embodiment, the first and second derived parameters can be created in steps 802 and 804. The first derived measurement accordingly can include LALS and MALS parameters. The second derived parameter can include DC and OP parameters. According to this embodiment, clustering in step 806 can include creating a scattergram with an axis based on the first and second derived parameters.

Other Example Embodiments

Other example embodiments of the present specification can include the identification and/or enumeration of immature granulocytes based on LALS and two or more parameters. Scattergrams, histograms, and/or other graphs types in two or more dimensions can be used in the differentiation and enumeration of the EGC population. For example, an embodiment can include the generation of a three dimensional surface image based on derived parameters and another physical or derived measurement, and the EGO population can be identified and enumerated based on the positions of the corresponding cell events in the three dimensional surface.

Figure 9:
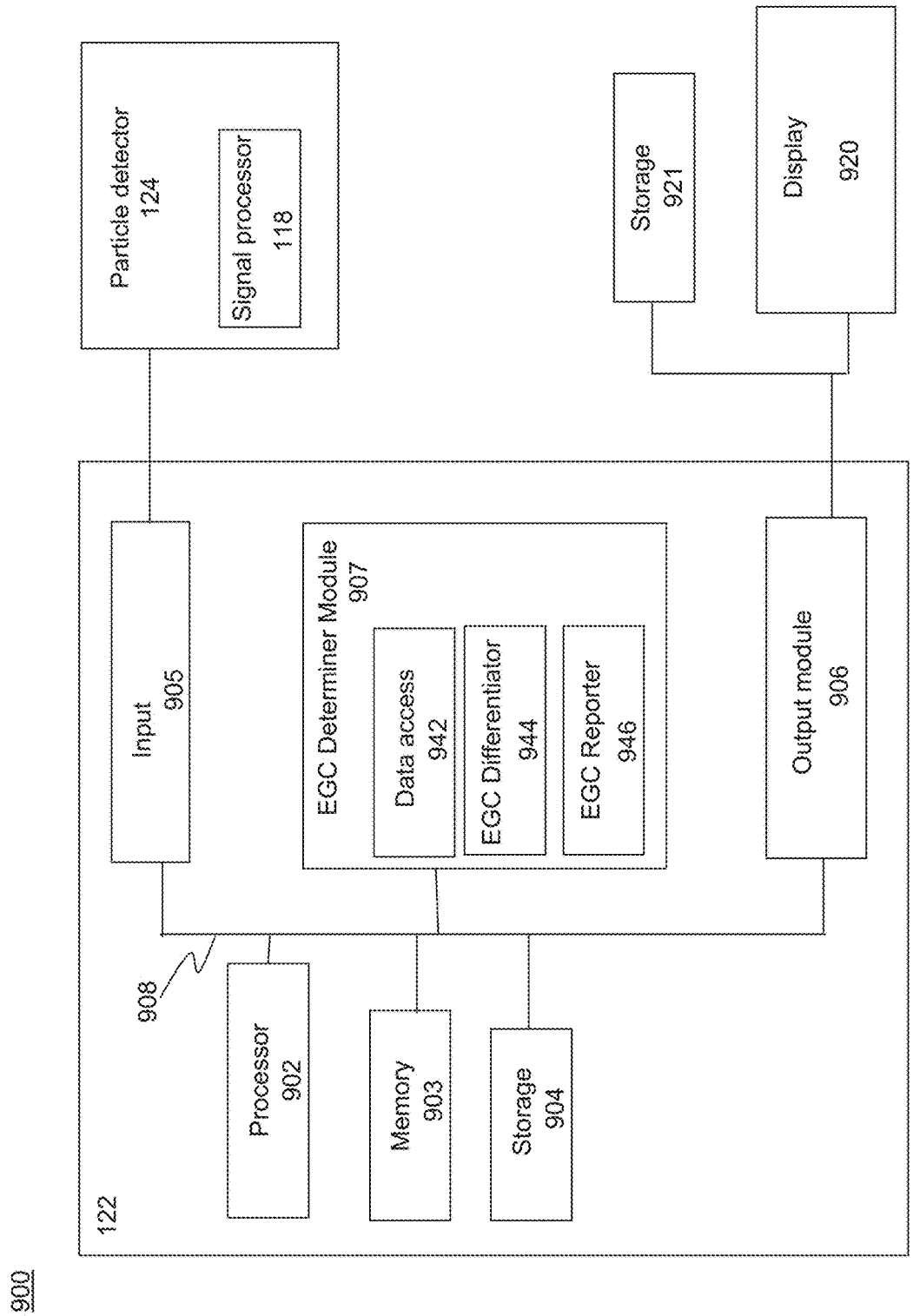
FIG. 9 shows a cellular event analyzer and a corresponding system according to an embodiment of the present specification.

FIG. 9 illustrates another embodiment of the present specification. A system 900 according to an embodiment of the present specification, includes a particle detector 124 coupled to an analyzer 122. Analyzer 122 may also be coupled to a display 920 and storage 921. Particle detector 124 detects particle events using one or more measurement parameters, and includes signal processor 118 that processes the detected measurement parameters to construct a signal for each particle event representing the duration of that particle in a measurement region. Signal processor 118, as noted above, generates cell events corresponding to the measurement of respective cells within the measurement region. Signal processor 118 can perform processing of the received signals to optimize the generation of cell events, for example, by reducing the noise in the received signals. The instructions for assembling the signal corresponding to the duration of a particle in the measurement region and the determining of the parameters corresponding to that signal can be implemented in any suitable programming language including a hardware description language (HDL), Assembly, C and C++, and may include one or more of hardware, firmware, or software components.

As described with respect to FIG. 1 above, analyzer 122 may either be located within particle analyzer 100 or be located separately coupled to particle detector 124 through a communications medium. Analyzer 122 receives cell event data corresponding to each particle detected by particle detector 124. The event data can include, among other things, parameters for LALS, OP, DC, and MALS.

Analyzer 122 includes components including a processor 902, a memory device 903, a storage device 904, an input device 905, an output device 906, an EGC determiner module 907 and a communications infrastructure 908. Processor 902 can be any microprocessor or other processor capable of executing processing instructions. Memory device 903 can include a random access memory. Storage device 904 includes a computer readable persistent storage medium such as a flash memory or hard disk. Processor 902 executes the instructions for receiving event data from particle analyzer, processing the received data and outputting the processed results data. Memory device 903 and storage device 904, provides any temporary or permanent memory and storage requirements of processor 902. Communication infrastructure 908 interconnects components of analyzer 122 to each other, and may include a communications medium, including but not limited to a peripheral component interconnect (PCI) bus, Extended Industry Standard Architecture (EISA) bus, Ethernet and/or WIFI. Input device 905 can include connectivity to particle analyzer 100 through communication infrastructure 908 and the capability to receive data including event data from particle analyzer 100.

EGC determiner module 907 includes the functionality to process the cell event data particle detector 124 to identify and enumerate EGC populations in the blood sample. For example, EGC determiner module 907 can include the instructions or a computer program to implement steps 708-716 of method 700. EGO determiner module 907 can comprise of a data access module 942, an EGO differentiator module 944, and an EGC reporter module 946. The data access module 942 can access the cellular event data received from the particle detector. Accessing the data can involve accessing a storage device to retrieve previously stored cell event data, or receiving cell event data real-time from a particle detector. The EGO differentiator module 944 can include the functionality to identify and enumerate the EGC population, for example, as described above in relation to steps 710 and 714 of method 700. The EGC reporter module can include the functionality to report the EGC information, for example, as described above in relation to steps 712 and 716 of method 700.

EGC determiner module 907 can be implemented in any suitable programming language including a hardware description language (HDL), Assembly, C and C++, and may include one or more of hardware, firmware, or software components. The instructions and/or computer program implementing the EGC determiner module 907 can, for example, be stored in computer readable storage medium 904.

Output module 906 includes the functionality to handle the cell population information including the EGC population information determined in the EGC determiner module 907 in a manner appropriate for the application. In one embodiment, output module 906 can generate one or more graphs according to preconfigured graph settings to display the differentiated cell populations determined in processing modules including EGO determiner module 907.

Output module 906 is coupled using a communications infrastructure 908 to display 920 and/or storage device 921. The results data from output module 906 is transmitted to display 920 to be displayed and analyzed by an operator. For example, display 920 may illustrate the results data in the form of a histogram, scattergram, or other form of graphic and/or textual display. In another embodiment, the results data may be stored in an external storage device 921 for subsequent processing and analysis.

In this disclosure, methods and systems were disclosed that can improve the diagnostic value of automated blood cell enumeration. In particular, embodiments of the present specification enable the automated identification and enumeration of EGCs in blood cell samples that can be critical for the detection and treatment of various conditions of infection. The disclosed methods and systems yield substantial improvements in cost effectiveness and efficiency over current methods and systems and can lead to significant improvements in the analysis of particle analyzer data.

The foregoing description of the specification has been presented for purposes of illustration and description. It is not intended to be exhaustive or to limit the specification to the precise form disclosed, and other modifications and variations may be possible in light of the above teachings. The embodiment was chosen and described in order to best explain the principles of the specification and its practical application to thereby enable others skilled in the art to best utilize the specification in various embodiments and various modifications as are suited to the particular use contemplated. It is intended that the appended claims be construed to include other alternative embodiments of the specification except insofar as limited by the prior art.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the methods, systems, and/or apparatus for identifying and/or enumerating early granulocyte cells.

Example 1

An evaluation of the enumeration of EGCs versus a reference 400 cell manual differential on a set of 1536 unique samples collected at seven different sites is shown below in Table 1. The correlation coefficient r was determined by comparing EGC % against the sum of promyelocytes %, myelocytes % and metamyelocytes %. The positive criterion used for the calculation of the area under the ROC curve was the sum of promyelocytes %, myelocytes % and metamyelocytes % being greater than or equal to 1%.

TABLE 1

Statistical Analysis EGC to Manual Reference Differential

| Samples | Samples meeting positive criteria | Correlation coefficient (r) | Area Under ROC Curve | Sensitivity | Specificity | Criterion for Sensitivity and Specificity |
|---|---|---|---|---|---|---|
| 1536 | 502 | 0.87 | 0.89 | 84.5 | 80.8 | >0.52 |

In the above example, 502 of the 1536 samples were scored by trained hematology technicians as containing EGCs. The same samples were then analyzed using DxH800 instrument programmed with the EGC detection protocol of the present specification. The correlation coefficient (r) was determined as a function of the number of samples scored by the instrument as containing EGCs in relation to the number of samples scored by the trained technicians.

Sensitivity is the ratio of true positive EGCs over true positive EGCs and false negative counts. Specificity, on the other hand, is the ratio of true negative EGCs over true negative EGCs and false positive counts. The area under ROC curve (receiver operating curve) is a measure of the accuracy of the analytical approach combining the sensitivity and the specificity of the EGC enumeration method. The criterion for listed sensitivity and specificity reflects the sliding scale of values trading sensitivity for specificity and vice versa. Thus, for example, a criterion of 1.0 would be where the specificity has been increased at the cost of a decrease in sensitivity. It is understood that the optimal value can be arrived at by a person of skill in the art.

A similar evaluation on a set of 315 samples collected using flow cytometry CD16 marker as a reference on two different sites provided the results show in Table 2. CD16 is a marker associated with neutrophils, but not EGCs. Thus, labeled CD16 antibodies can be used to gate neutrophils and separate them from the EGO population, which generally appears in a closely overlapping region of a scattergram to the neutrophil population. Less mature cells have less light scatter than mature cells. Thus, using a combination of CD16 antibodies and light scatter, EGCs populations can be gated. Using this method, 315 samples were screened and 164 of the samples were identified as containing EGCs. When the CD16 gating analyses approach was compared to the analytical method of the present specification, the present specification provided the results set forth in Table 2.

TABLE 2

Statistical Analysis EGG to Flow Cytometry CD16

| Samples | Samples meeting positive criteria | Correlation coefficient (r) | Area Under ROC Curve | Sensitivity | Specificity | Criterion for Sensitivity and Specificity |
|---|---|---|---|---|---|---|
| 315 | 164 | 0.90 | 0.90 | 82.3 | 80.8 | >0.50 |

Therefore, the present method has also demonstrated that the presence of cells with higher or lower levels of immaturity, such as blasts or juvenile Neutrophils (i.e., bands), has no significant impact on accuracy.

The above data analysis of the samples collected demonstrates that the present specification has high levels of correlation, sensitivity and specificity in comparison to the manual differential inspection of the samples.

The invention claimed is:

1. A method for enumerating early granulated cells (EGCs), comprising:
    analyzing unmodified white blood cells in a blood sample;
    discriminating the EGCs from other white blood cells (WBCs) based upon a first parameter and a second parameter, wherein the first parameter is low angle light scatter (LALS) and measures the distinct lobularity and/or surface structure properties of EGCs and wherein the second parameter comprises forward light scatter, side scatter, axial light loss (ALL), direct current (DC), radio frequency (RF), and/or opacity (OP);
    separating the discriminated EGCs from the other WBCs without the use of antibodies; and
    enumerating the discriminated population of EGCs.

2. The method of claim 1, wherein the low angle light scatter is combined with the second parameter for specificity and sensitivity in enumerating the discriminated population of the EGCs.

3. The method of claim 1, wherein the forward light scatter comprises upper medium angle light scatter (UMALS), lower medium angle light scatter (LMALS), and/or medium angle light scatter (MALS).

4. The method of claim 1, wherein the EGCs are enumerated with at least 85% sensitivity.

5. The method of claim 1, wherein the EGCs are enumerated with at least 80% specificity.

6. The method of claim 1, wherein the separating step comprises:
    clustering the analysis data to thereby generate a plurality of populations; and
    identifying the population of EGCs from the plurality of populations.

7. The method of claim 6, wherein the population of EGCs is substantially separated from a neutrophil population of the plurality of populations.

8. The method of claim 1, further comprising:
    enumerating the EGCs based upon the separated population of EGCs; and reporting the enumerated EGCs.

9. The method of claim 8, wherein the enumerated EGCs are reported as a percentage of a total number of white blood cells.

* * * * *